(12) United States Patent
Hess et al.

(10) Patent No.: US 11,504,312 B2
(45) Date of Patent: Nov. 22, 2022

(54) MOUTHRINSE FORMULATIONS

(71) Applicant: GABA International Holding GmbH, Therwil (CH)

(72) Inventors: Sylvia Hess, Holstein (CH); Ruth Hinrichs, Therwil (CH); Stephanie Jakumeit, Grenzach-Wyhlen (DE); Turan Matur, Binningen (CH); Andre Brunella, Dornach (CH); Peter Reiff, Lorrach-Haagen (DE)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/529,656

(22) PCT Filed: Dec. 18, 2015

(86) PCT No.: PCT/US2015/066642
§ 371 (c)(1),
(2) Date: May 25, 2017

(87) PCT Pub. No.: WO2016/100802
PCT Pub. Date: Jun. 23, 2016

(65) Prior Publication Data
US 2018/0021228 A1  Jan. 25, 2018

Related U.S. Application Data

(60) Provisional application No. 62/093,533, filed on Dec. 18, 2014.

(51) Int. Cl.
| | | |
|---|---|---|
| *A61K 8/21* | (2006.01) | |
| *A61Q 11/00* | (2006.01) | |
| *A61K 8/19* | (2006.01) | |
| *A61K 8/81* | (2006.01) | |

(52) U.S. Cl.
CPC .......... *A61K 8/21* (2013.01); *A61K 8/19* (2013.01); *A61K 8/8176* (2013.01); *A61Q 11/00* (2013.01)

(58) Field of Classification Search
None
See application file for complete search history.

(56) References Cited

U.S. PATENT DOCUMENTS

| | | |
|---|---|---|
| 2005/0271602 A1 | 12/2005 | Milanovich et al. |
| 2012/0207686 A1 | 8/2012 | Fruge et al. |

FOREIGN PATENT DOCUMENTS

| | | |
|---|---|---|
| RU | 2460512 | 9/2012 |
| WO | WO 1993/016680 | 9/1993 |
| WO | WO 1993/016681 | 9/1993 |
| WO | WO 1997/045096 | 12/1997 |
| WO | WO 2005/117820 | 12/2005 |
| WO | WO 2008/041055 | 4/2008 |
| WO | WO 2011/053291 | 5/2011 |
| WO | WO 2015/195139 | 12/2015 |

OTHER PUBLICATIONS

Claydon et al., 2001, "Studies on the effect of polyvinyl pyrrolidone on the activity of chlorhexidine mouthrinses: plaque and stain," Journal of Clinical Periodontology 28:558-564.
Claydon et al., 2001, "The effect of polyvinyl pyrrolidone on the clinical activity of 0.09 % and 0.2 % chlorhexidine mouthrinses," Journal of Clinical Periodontology 28:1037-1044.
Claydon et al., 2004, "Clinical study to compare tire effectiveness of a test whitening toothpaste with a commercial whitening toothpaste at inhibiting dental stain," Journal of Clinical Periodontology 31:1088-1091.
International Search Report and Written Opinion of the International Searchine Authority in International Application No. PCT/US2015/066642, dated Mar. 24, 2016.
Wade et al., 1997, "Studies on stannous flouride toothpaste and gel (1) Antimicrobial properties and staining potential in vitro," Journal of Clinical Periodontology 24:81-85.

*Primary Examiner* — Nannette Holloman

(57) ABSTRACT

An oral care mouth rinse composition containing at least one ionic tin source and polyvinylpyrrolidone wherein the polyvinylpyrrolidone is present in an amount of from 1.5 to 4 weight % based on the total weight of the oral care mouth rinse composition is provided.

6 Claims, No Drawings

MOUTHRINSE FORMULATIONS

CROSS REFERENCE TO RELATED APPLICATIONS

This application is a United States Application under 35 C.F.R. 371 claiming benefit of PCT Application No. PCT/US2015/066642, filed on Dec. 18, 2015, which claims priority benefit of U.S. Provisional Application No. 62/093,533, filed Dec. 18, 2014.

The present invention relates to oral care compositions comprising ionic tin and in particular to mouth rinse formulations comprising ionic tin.

BACKGROUND

Tin ions such as stannous ions are incorporated into oral care compositions including dentifrices and mouth rinses in order to provide a variety of oral care benefits including anticaries activity and for the treatment and/or prevention of gingivitis. However, the use of oral care compositions comprising ionic tin can lead to staining of the teeth and tongue in certain product users. It would therefore be desirable to be able to provide oral care compositions comprising tin ions that maintain beneficial oral care properties such as antibacterial activity, but result in reduced staining.

BRIEF SUMMARY

It has now surprisingly been discovered that incorporating polyvinylpyrrolidone into oral care mouth rinses comprising ionic tin can lead to a reduction in tooth staining without compromising oral care efficacy.

According to a first aspect of the present invention there is provided an oral care mouth rinse composition comprising
  (i) at least one source of ionic tin and
  (ii) polyvinylpyrrolidone
wherein the polyvinylpyrrolidone is present in an amount of from 1.5 to 4 weight % based on the total weight of the oral care mouth rinse composition.

Optionally the polyvinylpyrrolidone is present in an amount of from 2.20 to 3.00 weight % based on the total weight of the oral care mouth rinse composition. Further optionally the polyvinylpyrrolidone is present in an amount of from 2.20 to 2.50 weight % based on the total weight of the oral care mouth rinse composition. Further optionally the polyvinylpyrrolidone is present in an amount of from 2.30 to 2.45 weight % based on the total weight of the oral care mouth rinse composition.

Optionally the oral care mouth rinse comprises at least one stannous ion source, at least one stannic ion source or a combination thereof. Optionally the oral care mouth rinse comprises at least one stannous ion source. Optionally the at least one source of ionic tin is selected from the group comprising stannous fluoride, stannic fluoride, stannic chloride, stannic acetate, stannous chloride, stannous acetate and combinations thereof. Optionally the at least one source of ionic tin is selected from the group comprising stannous fluoride, stannous chloride, stannous acetate and combinations thereof.

Optionally the concentration of ionic tin is from 0.01 to 0.10 weight % based on the total weight of the oral care mouth rinse composition. Further optionally the concentration of ionic tin is from 0.02 to 0.08 weight % based on the total weight of the oral care mouth rinse composition. Further optionally the concentration of ionic tin is from 0.03 to 0.06 weight % or from 0.035 to 0.045 weight % based on the total weight of the oral care mouth rinse composition.

Optionally the at least one source of ionic tin comprises stannous fluoride.

Optionally the oral care mouth rinse composition further comprises a fluoride ion source which is not a tin salt, further optionally in an amount corresponding to 0.01 to 0.15 weight % fluoride based on the total weight of the composition. Further optionally the oral care mouth rinse composition comprises a fluoride ion source selected from sodium fluoride, potassium fluoride, sodium monofluorophosphate, sodium fluorosilicate, ammonium fluorosilicate, amine fluoride, ammonium fluoride and combinations thereof, even further optionally in an amount corresponding to 0.01 to 0.15 weight % fluoride based on the total weight of the composition.

Optionally the oral care mouth rinse composition comprises amine fluoride, sodium fluoride or a combination thereof. Further optionally the oral care mouth rinse composition comprises 0.02 to 0.08 weight % stannous fluoride and 0.010 to 0.50 weight % amine fluoride.

Optionally the oral care mouth rinse composition comprises 50 to 1500 ppm fluoride.

Optionally the oral care mouth rinse composition comprises polyvinylpyrrolidone having a molar mass of from 10,000 to 300,000 Daltons.

According to a further aspect of the present invention there is also provided a method to
  i. reduce or inhibit formation of dental caries,
  ii. reduce, repair or inhibit pre-carious lesions of the enamel,
  iii. reduce or inhibit demineralization and promote remineralization of the teeth
  iv. reduce hypersensitivity of the teeth,
  v. reduce or inhibit gingivitis,
  vi. promote healing of sores or cuts in the oral cavity,
  vii. reduce levels of acid producing bacteria
  viii. reduce or inhibit microbial biofilm formation in the oral cavity,
  ix. reduce or inhibit plaque formation in the oral cavity
  x. promote systemic health
  xi. clean teeth and oral cavity
the method comprising applying an effective amount of an oral care mouth rinse composition to the oral cavity of a subject in need thereof.

According to a further aspect of the invention there is also provided an oral care mouth rinse composition for use in a method to
  i. reduce or inhibit formation of dental caries,
  ii. reduce, repair or inhibit pre-carious lesions of the enamel,
  iii. reduce or inhibit demineralization and promote remineralization of the teeth
  iv. reduce hypersensitivity of the teeth,
  v. reduce or inhibit gingivitis,
  vi. promote healing of sores or cuts in the oral cavity,
  vii. reduce levels of acid producing bacteria
  viii. reduce or inhibit microbial biofilm formation in the oral cavity,
  ix. reduce or inhibit plaque formation in the oral cavity
  x. promote systemic health
  xi. clean teeth and oral cavity.

According to a further aspect of the invention there is also provided use of an oral care mouth rinse composition to
  i. reduce or inhibit formation of dental caries,
  ii. reduce, repair or inhibit pre-carious lesions of the enamel, iii. reduce or inhibit demineralization and promote remineralization of the teeth
iv. reduce hypersensitivity of the teeth,
v. reduce or inhibit gingivitis,
vi. promote healing of sores or cuts in the oral cavity,
vii. reduce levels of acid producing bacteria
viii. reduce or inhibit microbial biofilm formation in the oral cavity,
ix. reduce or inhibit plaque formation in the oral cavity
x. promote systemic health
xi. clean teeth and oral cavity
in a subject in need thereof.

According to a further aspect of the invention there is provided a method of reducing staining of surfaces in the oral cavity resulting from use of an oral care mouth rinse comprising at least one source of ionic tin, wherein the method comprises formulating the oral care mouth rinse composition to comprise polyvinylpyrrolidone in an amount of from 2.20 to 3.00 weight % based on the total weight of the oral care mouth rinse composition. Optionally the method comprises formulating the oral care mouth rinse composition to comprise from 2.30 to 2.45 weight % polyvinylpyrrolidone. Optionally the concentration of ionic tin in the oral care mouth rinse composition is from 0.02 to 0.08 weight % based on the total weight of the oral care mouth rinse composition.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention. The formulation may include a first feature described in one example configuration herein, as well as a second feature described in another example configuration herein. In other words, the invention contemplates mixing and matching features from the disclosed embodiments in various combinations.

DETAILED DESCRIPTION

The following description of the preferred embodiment(s) is merely exemplary in nature and is in no way intended to limit the invention, its application, or uses. The composition may include a first feature described in one example composition herein, as well as a second feature described in another example. In other words, the invention contemplates mixing and matching features from the disclosed embodiments in various combinations.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Polyvinylpyrrolidone (PVP), also known as polyvidone or povidone is a water-soluble polymer made from the monomer N-vinylpyrrolidone. Polyvinylpyrrolidone can have a molar mass of from 2,500 to 3,000,000 Daltons. In certain embodiments the PVP in the compositions of the invention has a molar mass of from 10,000 to 300,000 Daltons, for example 20,000 to 100,000 or 40,000 to 75,000. In certain embodiments the PVP has a molar mass of about 58,000 Daltons.

Without being limited by theory, it is thought that at the specific concentration of polyvinylpyrrolidone used in the compositions of the present invention, the PVP is surface active and acts as a film forming additive, inhibiting the formation of stains on the tooth surface.

The PVP is present in the oral care mouth rinse formulations of the present invention in an amount from 1.5 to 4 weight % based on the total weight of the composition. In certain embodiments, the PVP is present in an amount of from 2.20 to 3.00, 2.20 to 2.90, 2.20 to 2.80, 2.20 to 2.70, 2.20 to 2.60 or 2.20 to 2.50 weight % based on the total weight of the oral care mouth rinse composition. In certain embodiments, the PVP is present in an amount of from 2.20 to 2.45, 2.30 to 2.45 weight %, for example 2.4 weight %.

Mouth rinse (or mouthwash) compositions comprise one or more oral care active component in a liquid carrier. Typically, mouth rinse compositions are formulated suing a solvent such as water. They may be used to deliver oral care actives to the oral cavity of a consumer and may be used either before or after brushing and/or flossing.

The mouth rinse compositions of the present invention comprise a source of ionic tin. In certain embodiments the source of ionic tin is a source of stannous (Sn(II)) or stannic (Sn(IV)) ions. In certain embodiments the source of ionic tin comprises at least one stannous ion source, at least one stannic ion source or a combination thereof. In certain embodiments the source of ionic tin is a stannous ion source. In certain embodiments the source of ionic tin comprises a stannous salt. In certain embodiments the source of ionic tin is selected from water-soluble tin salts such as stannous fluoride, stannous chloride, stannic fluoride, stannic chloride, stannic acetate, stannous acetate and combinations thereof In certain embodiments the source of ionic tin is selected from stannous fluoride, stannous chloride, stannous acetate and combinations thereof. In certain embodiments the source of ionic tin comprises stannous fluoride, stannous chloride and/or combinations thereof. In certain preferred embodiments, the source of ionic tin is a stannous ion source. In particularly preferred embodiments the source of ionic tin is stannous fluoride. In certain embodiments separate soluble stannous and fluoride salts may be used to provide stannous fluoride in situ. Alternatively, stannous fluoride salt may be added to the composition directly.

In certain embodiments the concentration of ionic tin in the oral care mouth rinse composition is from 0.01 to 0.10 weight % based on the total weight of the oral care mouth rinse composition. In certain embodiments the concentration of ionic tin in the oral care mouth rinse composition is from 0.02 to 0.08 weight %, or from 0.03 to 0.06 weight %. In certain embodiments the concentration of ionic tin is about 0.04 weight % based on the total weight of the oral care mouth rinse composition.

In certain embodiments the mouth rinse compositions comprise a fluoride ion source which is not a tin salt i.e. a source of fluoride ions that is not a stannous or stannic salt. In certain embodiments the compositions of the invention comprise sodium fluoride, potassium fluoride, sodium monofluorophosphate, sodium fluorosilicate, ammonium fluorosilicate, amine fluoride, ammonium fluoride and/or a combination thereof. In certain embodiments the compositions of the invention comprise a fluoride ion source which is not a tin salt in an amount corresponding to 0.01 to 0.15 weight % fluoride based on the weight of the composition, for example from 0.01 to 0.14%, 0.01 to 0.12 weight % or 0.01 to 0.10 fluoride based on the weight of the composition. In certain embodiments the compositions of the invention comprise from 0.01 to 0.30 weight % sodium fluoride.

In certain embodiments the mouth rinse compositions comprise stannous fluoride and a source of fluoride ions that is not a stannous or stannic salt. For example, in certain embodiments, the mouth rinse compositions comprise stannous fluoride and amine fluoride.

In certain embodiments the composition comprises a total fluoride concentration sufficient to supply about 25 ppm to about 25,000 ppm fluoride ions, for example from about 500 ppm to about 10,000, from about 500 ppm to about 2000 ppm, or from about 1000 ppm to about 1600 ppm fluoride ions. In certain embodiments the non-stannous fluoride ion source is incorporated in an amount sufficient to supply from about 100 ppm to about 2000 ppm fluoride ions, for example from 200 to 500 ppm fluoride ions.

In certain embodiments, the mouth rinse composition comprises sodium fluoride, amine fluoride and/or a combination thereof. In certain embodiments the composition comprises OLAFLUR (N,N,N'-tris(2-hydroxyethyl)-N'-octadecyl-1,3-diaminopropane dihydrofluoride) or DECTAFLUR (9-octadecenylamine-hydrofluoride) in an amount of from 0.10 to 0.25 weight %.

In certain embodiments, the mouth rinse composition comprises a combination of a source of ionic tin and amine fluoride, for example stannous fluoride and amine fluoride. In certain embodiments the mouth rinse composition comprises stannous fluoride and OLAFLUR (N,N,N'-tris(2-hydroxyethyl)-N'-octadecyl-1,3-diaminopropane dihydrofluoride). In certain embodiments, the composition comprises 0.10 to 0.25 weight % amine fluoride and 0.01 to 0.10 weight % ionic tin. In certain embodiments the compositions comprises 0.10 to 0.25 weight % amine fluoride and 0.013 to 0.130 weight % stannous fluoride.

In certain embodiments the compositions of the invention may also comprise a salt of pyrrolidone carboxylic acid (also known as PCA, 2-pyrrolidone-5-carboxylic acid; 5-oxoproline; pidolic acid or pyroglutamic acid). In certain embodiments the compositions of the invention may comprise a salt of the L-enantiomer of pyrrolidone carboxylic acid, for example zinc pyrrolidone carboxylate, copper pyrrolidone carboxylate, magnesium pyrrolidone carboxylate or manganese pyrrolidone carboxylate. In certain embodiments the compositions of the invention may comprise zinc L-pyrrolidone carboxylate. The salt of pyrrolidone carboxylic acid may be present in an amount of from 0.01 to 0.75 weight %, for example from 0.05 to 0.50 weight %, 0.075 to 0.40 weight %, 0.09 to 0.30 weight % or 0.10 to 0.20 weight % based on the total weight of the composition.

In any of the above embodiments, the compositions may further comprise a flavoring agent. The flavoring agent may comprise one or more essential oils as well as various flavoring aldehydes, esters and/or alcohols. In certain embodiments, the flavoring agent comprises one or more essential oil selected form oils of peppermint, wintergreen, sassafras, clove, sage, eucalyptus, marjoram, cinnamon, lemon, lime, grapefruit and orange. In certain embodiments, the flavoring agent comprises oils of peppermint and spearmint. In certain embodiments the composition comprises from 0.05 to 3.0 weight %, 0.05 to 2.0 weight % or 0.08 to 2.0 weight % flavoring agent based on the total weight of the composition.

In any of the above embodiments, the compositions may further comprise at least one surfactant. Any orally acceptable surfactant such as a nonionic, anionic or amphoteric surfactant may be used. Optionally a surfactant may be present in an amount of from 0.01 weight % to 10 weight %, for example from 0.05 to 5 weight % or from 0.10 to 2.0 weight % based on the total weight of the composition.

In any of the above embodiments, the compositions may further comprise a sweetener such as, for example, sodium saccharin. One or more sweeteners may be present in an amount of from 0.005 weight % to 5 weight % based on the total weight of the composition, for example, 0.01 weight % to 0.1 weight % or 0.01 to 0.05 weight %.

In any of the above embodiments, the compositions may further comprise at least one colorant. Colorants may include pigments, dyes, lakes and agents imparting a particular luster or reflectivity such as pearling agents. Any orally acceptable colorant can be used. One or more colorants may optionally be present in the compositions in an amount of from 0.0001 weight % to 20 weight %, for example from 0.0001 weight % to 1 weight % or from about 0.0001 weight % to 0.5 weight % based on the total weight of the composition.

In any of the above embodiments, the compositions may further comprise a polyhydric alcohol such as glycerine, sorbitol, xylitol, propylene glycol and combinations thereof. In certain embodiments the compositions may optionally comprise from about 0.10 to about 10 weight % polyhydric alcohol based on the total weight of the composition. In certain embodiments the compositions may comprise from 0.50 to 10 weight % xylitol, for example from 0.50 to 7.0 weight % xylitol. In certain embodiments the compositions may comprise from 0.50 to 5.0 weight % glycerine, for example 1.0 to 3.5 weight % glycerin. In certain embodiments the compositions may comprise 0.10 to 1.00 weight % propylene glycol. In any of the above embodiments, the compositions may comprise 0.50 to 7.0 weight % xylitol and 1.0 to 3.5 weight % glycerin based on the total weight of the composition.

In any of the above embodiments, the compositions may further comprise one or more polymers selected from polyethylene glycols, polyvinylmethyl ether maleic acid copolymers and polysaccharides (e.g. cellulose derivatives such as carboxymethyl cellulose or microcrystalline cellulose, hydroxyethyl cellulose, or polysaccharide gums such as xanthan gum, carrageenan gum or chitosan). Such polymers may be present in any of the compositions of the invention in an amount of from 0.05 to 5.0 weight %.

EXAMPLES

Example 1

Staining Study

Staining studies were carried out using both white PMMA and human enamel. Black tea was used as a staining agent. White PMMA samples of thickness 3 mm were prepared and cleaned with ethanol. Human retained third molars were prepared by storage in 7% hydrogen peroxide for 24 hours, separating the roots from the crowns and sectioning the crowns in half.

Staining experiments were carried out at room temperature (25° C.). Samples were exposed to saliva, mouth rinse, black tea or storage medium. Pre-treatment with human unstimulated saliva for 30 minutes was used to initiate pellicle formation. A black tea solution was prepared using Marks & Spencer Extra Strong Tea Leaves (3 g in 100 ml freshly boiled distilled water for 5 minutes). This was filtered through gauze and stored for use at 50° C.

After pre-treatment with saliva, samples were submitted to a cyclic treatment comprising exposure to
1. human saliva (2 minutes)
2. distilled water rinse
3. mouth rinse (30 s)
4. distilled water rinse
5. black tea (1 minute)
6. distilled water rinse
7. storage in HEPES buffer Steps 1 to 8 were repeated for 8 cycles, and optical measurements of the specimens then taken using an intra-oral dental spectrophotometer (Easyshade, VITA).

Color changes were characterized using the Commission Internationale d'Eclairage L*C*h* color space. The L*C*h* system is based on three color receptors (red, green and blue) and allows specification within a three dimensional space. The L* axis represents the degree of lightness within ranges from 0 (black) to 100 (white). Chroma (C*) describes the saturation of a color and is measured as the distance from the vertical axis. Hue (h*) is the angle of displacement. Measurements were used to calculate:

$\Delta L = L^*_0 - L^*_x$ where $L^*_0$ is lightness before staining and $L^*_x$ is lightness after staining for x cycles $\Delta C = C^*_0 - C^*_x$ where $C^*_0$ is color saturation before staining and $C^*_x$ is color saturation after staining for x cycles $\Delta h = h^*_0 - h^*_x$ where $h^*_0$ is hue angle before staining and $h^*_x$ is h after staining for x cycles a* and b* are then calculated by $a^* = C^* \cdot \cos(h^*)$ and $b^* = C^* \cdot \sin(h^*)$, $|\Delta a = a^*_0 - a^*_x|$ and $|\Delta b = b^*_0 - b^*_x|$. $\Delta E$ (color change of the specimens) is then calculated using $\Delta E = \sqrt{[(\Delta L^*)^2 + (\Delta a^*)^2 + (\Delta b^*)^2]}$.

Formulations A and B (Table 1) were tested for their propensity to stain PMMA and human enamel.

TABLE 1

| | Formulation A weight % based on total weight of composition | Formulation B weight % based on total weight of composition |
|---|---|---|
| Xylitol | 0.850 | 0.850 |
| PVP (MW 58,000) | 0.300 | 2.400 |
| Stannous fluoride | 0.054 | 0.054 |
| Amine fluoride | 0.170 | 0.170 |
| Emulsifier | 0.250 | 0.250 |
| Water, aroma, sweetener and color | QS | QS |

The mouth rinse formulations are prepared by mixing water, powdered ingredients, colorants and PVP in a vessel and stirring to dissolve. Stannous fluoride is dissolved in concentrated amine fluoride solution and added to the vessel. This mixture is stirred until homogeneous. Aroma, surfactants and all other remaining ingredients are added and the mixture stirred until the solution is clear. If necessary, the pH is adjusted. The mouth rinse formulations were then used in a staining study as outlined above and $\Delta E$ values calculated. Staining experiments were repeated six times on nine separate occasions and the average $\Delta E$ calculated.

TABLE 2

| Formula | PVP wt. % | Average $\Delta E$ |
|---|---|---|
| A | 0.30 | 21.04 |
| B | 2.40 | 13.27 |

Formulation A (a commercially available stannous containing mouth rinse comprising 0.30% PVP) was shown to result in greater staining (higher value of $\Delta E$) than an equivalent formulation (B) comprising 2.4% PVP. The inclusion of 2.4 weight % PVP led to a significant drop in $\Delta E$, demonstrating the reduced staining of this composition.

Example 2

Further Staining Study

Formulations C (identical to Formula A above) and D-I (Table 3) were tested for their propensity to stain PMMA. Formulations D-I are the same as Formulas A and C, except for the amount of PVP. The procedure used was the same as described above, except that Staining experiments were repeated three times on three separate occasions and the average $\Delta E$ calculated.

TABLE 3

| | Formulations (weight % based on total weight of composition) | | | | | | |
|---|---|---|---|---|---|---|---|
| Ingredient | C | D | E | F | G | H | I |
| Xylitol | 0.850 | 0.850 | 0.850 | 0.850 | 0.850 | 0.850 | 0.850 |
| PVP (MW 58,000) | 0.3 | 1.5 | 2.2 | 2.8 | 3.0 | 3.5 | 4.0 |
| Stannous fluoride | 0.054 | 0.054 | 0.054 | 0.054 | 0.054 | 0.054 | 0.054 |
| Amine fluoride | 0.170 | 0.170 | 0.170 | 0.170 | 0.170 | 0.170 | 0.170 |
| Emulsifier | 0.250 | 0.250 | 0.250 | 0.250 | 0.250 | 0.250 | 0.250 |
| Water, aroma, sweetener and color | QS | QS | QS | QS | QS | QS | QS |

TABLE 4

| Formula | PVP wt. % | Average $\Delta E$ |
|---|---|---|
| C | 0.3 | 21.33 |
| D | 1.5 | 17.76 |
| E | 2.2 | 15.95 |
| F | 2.8 | 14.42 |
| G | 3.0 | 14.80 |
| H | 3.5 | 16.61 |
| I | 4.0 | 12.40 |

Formulations C-I demonstrate the correlation between PVP concentration and reduced staining (lower value of $\Delta E$). The inclusion of PVP led to a concentration-dependent drop in $\Delta E$, in the range of 1.5-4%.

What is claimed is:
1. An oral care mouth rinse composition comprising:
   (i) at least one source of ionic tin, wherein the at least one source of ionic tin comprises 0.03 to 0.06 weight % stannous fluoride,
   (ii) polyvinylpyrrolidone having a molecular mass of about 58,000 Daltons, which is present in an amount of from 2.30 to 2.45 weight %, based on the total weight of the oral care mouth rinse composition;
   (iii) 0.010 to 0.50 weight % amine fluoride based on the total weight of the oral care mouth rinse composition;
   (iv) 0.5 to 7 weight % xylitol;
   (v) 0.0001 weight % to 0.5 weight % of a colorant;

(vi) 0.01 weight % to 0.1 weight % of a sweetener;
(v) an emulsifier; and
(vi) water.

2. The oral care mouth rinse composition of claim 1 further comprising a fluoride ion source selected from sodium fluoride, potassium fluoride, sodium monofluorophosphate, sodium fluorosilicate, ammonium fluorosilicate, ammonium fluoride and combinations thereof, optionally in an amount corresponding to 0.01 to 0.15 weight % of fluoride based on the total weight of the composition.

3. The oral care mouth rinse composition of claim 1 further comprising sodium fluoride.

4. The oral care mouth rinse composition of claim 1 comprising 50 to 1500 ppm fluoride.

5. An oral care mouth rinse composition according to claim 1 for use in a method to
 (i) reduce or inhibit formation of dental caries,
 (ii) reduce, repair or inhibit pre-carious lesions of the enamel,
 (iii) reduce or inhibit demineralization and promote remineralization of the teeth,
 (iv) reduce hypersensitivity of the teeth,
 (v) reduce or inhibit gingivitis,
 (vi) promote healing of sores or cuts in the oral cavity,
 (vii) reduce levels of acid producing bacteria,
 (viii) reduce or inhibit microbial biofilm formation in the oral cavity,
 (ix) reduce or inhibit plaque formation in the oral cavity,
 (x) promote systemic health, or
 (xi) clean teeth and oral cavity.

6. The oral care mouth rinse composition of claim 1 having the composition:

| Component | Weight % based on Total Weight of the Composition |
| --- | --- |
| Xylitol | 0.850 |
| PVP (MW 58,000) | 2.40 |
| Stannous Fluoride | 0.054 |
| Amine Fluoride | 0.170 |
| Emulsifier | 0.250 |
| Water, Aroma, Sweetener and Color | QS. |

* * * * *